United States Patent [19]
Schehlmann et al.

[11] Patent Number: 6,080,811
[45] Date of Patent: Jun. 27, 2000

[54] ADHESIVES FOR DENTAL PROSTHESES

[75] Inventors: Volker Schehlmann, Römerberg; Reinhold Dieing, Schifferstadt; Axel Sanner, Frankenthal, all of Germany

[73] Assignee: BASF Aktiengesellschaft, Ludwigshafen, Germany

[21] Appl. No.: 09/017,774

[22] Filed: Feb. 2, 1998

[30] Foreign Application Priority Data

Feb. 5, 1997 [DE] Germany .............................. 197 04 293

[51] Int. Cl.⁷ .............................. C08L 31/00; C08L 33/00; C08L 33/06; C09K 3/00
[52] U.S. Cl. ...................... 524/556; 524/560; 523/105; 523/120; 106/35; 433/229
[58] Field of Search ..................................... 524/556, 560; 523/105, 120; 106/35; 433/229

[56] References Cited

U.S. PATENT DOCUMENTS 4,542,168  9/1985  Chang et al. ............................ 523/118

FOREIGN PATENT DOCUMENTS 122481  10/1984  European Pat. Off. .
265916   5/1988  European Pat. Off. .

*Primary Examiner*—Nathan M. Nutter
*Attorney, Agent, or Firm*—Keil & Weinkauf

[57] ABSTRACT

Adhesives for dental prostheses, comprising a) as active adhesive ingredient partially or completely neutralized copolymers of from 5 to 95% by weight, based on the copolymer, of one or more acrylic esters of the formula I $$CH_2=CR'—COOR \qquad \text{I (monomer A)},$$

where R' is hydrogen or methyl and R is alkyl of 1 to 30 C atoms, and from 95 to 5% by weight of methacrylic and/or acrylic acid (monomer B), and b) a vehicle which is customary in adhesives for dental prostheses.

10 Claims, No Drawings

ADHESIVES FOR DENTAL PROSTHESES

BACKGROUND OF THE INVENTION

1. Field of the Invention

The invention relates to adhesives for dental prostheses, which comprise as active adhesive ingredient at least partially neutralized copolymers of acrylates or methacrylates and acrylic or methacrylic acid together with conventional vehicles.

2. Description of the Related Art

Adhesives for dental prostheses are used to adapt, or at least help to adapt, the denture to the mucous membrane of the soft palate tissue and to the gingival grooves, with a close, firm fit. The adhesive is applied to the moistened denture, which is then inserted into the mouth. The saliva wets the surface of the layer of adhesive, causing it to swell and at the same time developing the adhesive force.

Critical parameters are the adhesive force and duration of adhesion. In this context, the mechanisms responsible for the holding effect are highly complex. The viscosity of the vehicle base and, consequently, of the finished product plays an important part. Substances used as vehicle base include mineral oil (paraffin oil), vaseline (petrolatum) and waxes, which are diluted if required with polyethylene glycol or glycerol and which make up in total from about 20 to 60% of the finished product. The viscosity is determined primarily by the overall formulation; that is, by the totality of the active substances and vehicle substances in the adhesive. A large number of compositions exist, each tailored to particular uses.

Very good adhesive force is shown by those dental-prosthesis adhesives, known from numerous patents, for example EP-A 0 122 481 and EP-A 0 265 916, whose active adhesive compositions comprise copolymers of vinyl methyl ethers and maleic acid which have been partially or completely neutralized. Suitable salts in this context are alkali metal, alkaline earth metal or zinc salts.

The preparation of these copolymers, however, generally requires an organic solvent which has to be removed again at great technical expense. In spite of this expense its removal is in many cases not quantitative, so that in some cases residues of solvent remain in the end products. This is undesirable.

U.S. Pat. No. 4,542,168, moreover, discloses the use, as active adhesive substances, of crosslinked and partially neutralized polyacrylic acid together with at least one hydrophilic polymer. These adhesives for dental prostheses have the disadvantage that their adhesive force is still not entirely satisfactory and that they are likewise prepared in organic solvents which are still detectable in the product.

BRIEF SUMMARY OF THE INVENTION

It is an object of the present invention to provide dental-prosthesis adhesives in which the active substances comprise copolymers which further increase the adhesive force of the adhesives and which can be prepared preferably without solvent.

We have found that the object of the invention is achieved by adhesives for dental prostheses, which comprise a) as the composition which activates the adhesion, partially or completely neutralized copolymers of from 5 to 95% by weight, based on the copolymer, of one or more acrylic esters of the formula I

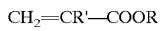       I (monomer A), where R' is hydrogen or methyl and R is alkyl of 1 to 30, preferably 1 to 4, C atoms, and from 95 to 5% by weight of methacrylic and/or acrylic acid (monomer B), and b) a vehicle which is customary in adhesives for dental prostheses.

Preferred compositions (a) which activate the adhesion are those comprising from 20 to 80% by weight of ethyl acrylate and methyl methacrylate and from 80 to 20% by weight of methacrylic or acrylic acid. Specific examples which may be mentioned are copolymers comprising approximately 50% by weight of ethylene acrylate and approximately 50% by weight of acrylic acid, for example Eudragit® L (Röhm) or Kollicoat® MAE 30 (BASF) or copolymers comprising approximately 67% by weight of methyl methacrylate and 33% by weight of methacrylic acid, for example Eudragit® S (RÖHM).

The copolymers (a) may also comprise minor amounts, for example up to 30% by weight, based on the copolymer, of further monomers C in copolymerized form, such as acrylamides, methacrylamides, N-vinyllactams, hydroxyalkyl acrylates, crotonic acid or maleic acid.

The copolymers (a) must be at least partially neutralized. In general, from 30 to 95 mol-%, preferably from 30 to 80 mol-% and, with particular preference, from 35 to 75 mol-% of the free carboxyl groups of the copolymer have been neutralized to the alkali metal, alkaline earth metal or zinc salts. The salts can be uniform or mixed salts. Preference is given to sodium, calcium, magnesium, strontium or zinc salts.

The copolymers in general have a molecular weight from 30,000 to 5 million, preferably from 100,000 to 3 million daltons, so that in the form of at least partly neutralized salts they are soluble or at least swellable in water. Their suitable properties, especially the viscosity, can be controlled by way of the preparation process and the optimum choice of salts, with a higher proportion of divalent metals leading in general to an increased solvent viscosity.

The copolymers are prepared in a manner known per se by solution polymerization or, preferably, by suspension or emulsion polymerization in water. Particular preference is given to emulsion polymerization.

In the emulsion polymerization described in more detail below, ionic and/or nonionic emulsifiers and/or protective colloids and stabilizers are used as surface-active compounds.

A detailed description of suitable protective colloids is given in Houben-Weyl, Methoden der organischen Chemie, Volume XIV/1, Makromolekulare Stoffe, Georg Thieme Verlag, Stuttgart, 1961, pp. 411 to 420. Suitable emulsifiers include anionic, cationic and nonionic emulsifiers. The accompanying surface-active substances employed are, preferably, exclusively emulsifiers, whose molecular weights—in contradistinction to the protective colloids—are usually below 2000 g/mol. Where mixtures of surface-active substances are used the individual components must of course be compatible with one another, which in case of doubt can be checked on the basis of a few preliminary experiments. It is preferred to use anionic and nonionic emulsifiers as surface-active substances. Examples of customary co-emulsifiers are ethoxylated fatty alcohols (EO units: 3 to 50, alkyl: $C_8$- to $C_{36}$), ethoxylated mono-, di- and trialkylphenols (EO units: 3 to 50, alkyl: $C_4$- to $C_9$), ethoxylated sorbitan esters (EO units: 5 to 30; saturated and unsaturated $C_{12}$–$C_{30}$ fatty acids), ethoxylated castor oils (EO units: 5 to 80, hydrogenated and unhydrogenated), alkali metal salts of dialkyl esters of sulfosuccinic acids, and alkali metal salts and ammonium salts of alkyl sulfates (alkyl: $C_8$- to $C_{12}$), of ethoxylated alkanols (EO units: 4 to 30, alkyl: $C_{12}$- to $C_{18}$), of ethoxylated alkylphenols (EO units: 3 to 50, alkyl: $C_4$- to $C_9$), of alkylsulfonic acids (alkyl: $C_{12}$- to $C_{18}$) and of alkylarylsulfonic acids (alkyl: $C_6$- to $C_{18}$).

Further suitable emulsifiers are compounds of the formula II

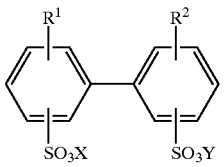

(II)

where $R^1$ and $R^2$ are hydrogen or $C_4$- to $C_{14}$-alkyl but are not simultaneously hydrogen, and X and Y can be alkali metal ions and/or ammonium ions. Preferably, $R^1$ and $R^2$ are hydrogen or linear or branched alkyl having 6 to 18 C atoms, in particular 6, 12 or 16 C atoms, and again are not both simultaneously hydrogen. X and Y are preferably sodium, potassium or ammonium ions, particular preference being given to sodium. Particularly advantageous compounds II are those in which X and Y are sodium, $R^1$ is branched alkyl having 12 C atoms and $R^2$ is hydrogen or $R^1$. It is common to use technical-grade mixtures comprising a proportion of from 50 to 90% by weight of the monoalkylated product, an example being Dowfax® 2A1 (trade mark of Dow Chemical Company).

Suitable emulsifiers are also given in Houben-Weyl, loc. cit., pp. 192 to 208.

Commercial names of emulsifiers are, for example, Dowfax® 2A1, Emulan® NP 50, Dextrol® OC 50, Emulgator 825, Emulgator 825 S, Emulan® NP OG, Texapon® NSO, Nekanil® 904 S, Lumiten® I-RA, Lumiten® E 3065, Diponil® FES 77, Lutensol® AT 18, Steinapol® VSL, Emulphor® NPS 25, Cremophor® RH 40, Tween® 80.

The surface-active substance is usually used in amounts of from 0.1 to 10% by weight, based on the monomers to be polymerized.

Examples of water-soluble initiators for the emulsion polymerization are ammonium salts and alkali metal salts of peroxodisulfuric acid, for example sodium peroxodisulfate, hydrogen peroxide, or organic peroxides, for example tert-butyl hydroperoxide.

Those systems known as reduction/oxidation (redox) initiator systems are particularly suitable.

The redox initiator systems consist of at least one, usually organic, reducing agent and of an inorganic or organic oxidizing agent.

The oxidizing component comprises, for example, the abovementioned initiators for emulsion polymerization.

The reducing components comprise, for example, alkali metal salts of sulfurous acid, such as sodium sulfite, sodium hydrogen sulfite, alkali metal salts of disulfurous acid, such as sodium disulfite, bisulphite addition compounds of aliphatic aldehydes and ketones, such as acetone bisulfite, or reducing agents such as hydroxymethanesulfinic acid and its salts or ascorbic acid. The redox initiator systems can be used in conjunction with soluble metal compounds whose metallic component is able to occur in a plurality of valence states.

Examples of customary redox initiator systems are ascorbic acid/iron(II) sulfate/sodium peroxodisulfate, tert-butyl hydroperoxide/sodium disulfite, tert-butyl hydroperoxide/ Na hydroxymethanesulfinate. The individual components, for example the reducing component, can also be mixtures, for example a mixture of the sodium salt of hydroxymethanesulfinic acid and sodium disulfite.

The abovementioned compounds are usually employed in the form of aqueous solutions, the lower concentration being determined by the amount of water which is acceptable in the dispersion and the upper concentration by the solubility of the compound concerned in water. In general the concentration is from 0.1 to 30% by weight, preferably from 0.5 to 20% by weight and, with particular preference, from 1.0 to 10% by weight, based on the solution.

The amount of the initiators is in general from 0.1 to 10% by weight, preferably from 0.5 to 5% by weight, based on the monomers to be polymerized. It is also possible to use two or more different initiators in the emulsion polymerization.

Regulators can be employed in the course of the polymerization, in amounts, for example, of from 0 to 0.8 parts by weight per 100 parts by weight of the monomers to be polymerized; these regulators reduce the molar mass. Examples of suitable regulators are compounds having a thiol group, such as tert-butyl mercaptan, ethylhexyl thioglycolate, mercaptoethanol, mercaptopropyltrimethoxysilane or tert-dodecyl mercaptan. The regulators do not contain any polymerizable, ethylenically unsaturated group. They bring about termination of polymer chain growth and are therefore attached to the polymer chains at their ends.

The emulsion polymerization takes place generally at from 30 to 130° C., preferably from 50 to 90° C. The polymerization medium can consist either of water alone or of mixtures of water with water-miscible liquids, such as methanol. It is preferred to use water alone. The emulsion polymerization can be conducted either as a batch process or else in the form of a feed technique, including a stepwise or gradient procedure. Preference is given to the feed technique, in which a portion of the polymerization mixture is charged to the reactor, this initial charge is heated to the polymerization temperature and polymerization is begun, and then the remainder of the polymerization mixture is fed to the polymerization zone, continuously, in stages or under a concentration gradient, usually by way of two or more spatially separate feed streams, of which one or more comprise the monomers in pure or in emulsified form, during which the polymerization is maintained. It is also possible to initially introduce a seed polymer in the polymerization, for the purpose, for example, of better establishing the particle size.

The manner in which the initiator is added to the polymerization vessel in the course of the free-radical aqueous emulsion polymerization is known to the person of average skill in the art. It can either be included entirely in the initial charge to the polymerization vessel or deployed continuously or in stages in the course of the free-radical aqueous emulsion polymerization, at the rate at which it is consumed. In each individual case this will depend, as is known to the person of average skill in the art, both on the chemical nature of the initiator system and on the polymerization temperature. It is preferred to include a portion in the initial charge and to feed the remainder to the polymerization zone at the rate at which it is consumed.

In order to remove the residual monomers it is also usual to add initiator after the end of the actual emulsion polymerization, in other words after at least 95% conversion of the monomers.

The individual components can, in the case of the feed technique, be supplied to the reactor from above, through the side or from below, through the reactor floor.

The emulsion polymerization produces aqueous solutions or dispersions of the polymer, in general with solids contents of from 15 to 75% by weight, preferably from 25 to 60% by weight.

The resulting copolymers are then converted, in whole or in part, to the salt form.

This is done by adding basic inorganic salts, for example hydroxides, oxides, phosphates, carbonates, hydrogen carbonates, acetates or formates of the alkali metal or alkaline earth metals or of zinc after the polymerization or even during it. It is preferred to use the oxides and hydroxides.

The methods of neutralization, that is of converting carboxyl-containing polymers to the salts, are known per se and are described, for instance, in U.S. Pat. No. 5,037,924, Example 3. A technically advantageous method is described in EP-A 03 15 015, the content of which is incorporated herein by reference.

According to a preferred procedure, the aqueous polymer solution or dispersion is introduced first of all and the inorganic salt, in powder form, is introduced in portions in the desired amount and composition. Prior to the subsequent drying operation it is possible if desired to supply further additives. In principle, however, it is also possible to dry the unneutralized copolymer and then to add the inorganic salt.

Depending on the proportion of acrylic and/or methacrylic acid, in other words on the number of carboxyl groups in the copolymer, and on the degree of neutralization, either a polymer dispersion or an aqueous polymer solution is obtained; to produce the adhesives this dispersion or solution is dried so that it can be processed with the vehicle (b) to the finished adhesive.

Drying takes place by methods known per se, for example in fluidized bed dryers or, preferably, by spray drying. In the course of this drying it may be found judicious to adjust the moisture content of the dried product so as to give a residual moisture content of up to 10% by weight, as described in DE-A 21 33 709. It has also been found judicious to maintain certain particle sizes of the dried copolymer, for example of less than 250$\mu$, preferably 5 to approximately 200$\mu$; in other words, sieving or grinding may be necessary.

Compounding of the copolymer (a) with the vehicle (b) takes place in a customary manner by mechanical incorporation at below 500C. During compounding it is possible to incorporate as well additives which do not impair the adhesive force of the compositions, such as flavors, thickeners such as silica powder, or colorants.

The vehicle component (b) comprises, generally as main constituents, a mineral oil such as liquid paraffin, or vaseline such as petrolatum, with or without viscosity regulators such as polyethylene glycol or glycerol or low molecular mass polyethylene. The mineral oil having the required viscosity is preferably a highly refined white oil having a viscosity of 50 to 350 mpas at 38° C. The low molecular mass polyethylene has a molecular weight of, for example, from 1000 to 21,000, preferably from 2000 to 5000, as measured by gel permeation chromatography. Pulverulent polyethylene polymers having a mean molecular weight of approximately 2000 are particularly preferred. The proportion of the vehicle (b) in the finished adhesive composition is in general from 0.1 to 60% by weight.

It is possible in principle to do without the use of oils in the dental prosthesis adhesives if, for example, the intention is to prepare an adhesive powder.

To the copolymers (a) before or after drying, or else to the finished mixture of (a) and the vehicle (b), it is possible to add further active adhesive substances or additives which improve the other properties of the prosthesis adhesives, such as conventional alkyl vinyl ether maleic anhydride copolymer partial salts, sodium carboxymethylcellulose, polyethylene oxide, karaya gum, polyethylene glycol, sodium alginate, hydroxyethylcellulose, chitosan, guar gum, Carbopol polymers, polyvinyl alcohol, polyvinylpyrrolidone, copolymers of vinylpyrrolidone and vinyl acetate, polysaccharides or chemically modified polysaccharides, or other substances known to the skilled worker which are active in terms of adhesion.

The new dental prosthesis adhesives can additionally be coated, as described in EP-A 00 73 850, in order to increase the duration of adhesion, with retarded release of the adhesion-active compositions.

The novel dental prosthesis adhesives are distinguished by improved adhesive force, very simple preparation and physiological acceptability.

Certain copolymers (a) are already known, in unneutralized form and with addition of alkali, from EP-A 0 403 959 and DE-A 3 208 791 as tablet-coating materials with controlled solubility or swellability in the gastrointestinal tract.

In addition, U.S. Pat. No. 4,529,748 discloses the use of unneutralized poly[methacrylic acid, methyl methacrylate 1.2] as a coating on Na carboxymethylcellulose in dental prosthesis adhesives with the aim, through the gradual dissolution of the coating, of releasing fresh adhesive in the form of the Na carboxymethylcellulose and thus of increasing the duration of adhesion. The use in accordance with the invention of the at least partially neutralized carboxyl-containing copolymers as the active adhesive substance is neither described nor suggested thereby.

EXAMPLES

Example 1

(Preparing the copolymers (a))

From 1 g of sodium lauryl sulfate, 6.7 g of a customary commercial nonionic emulsifier, 100 g of water, 1.3 g of ethylhexyl thioglycolate and 300 g of monomer mixture an emulsion was prepared which was added by the feed technique and over the course of from about 2 to 4 hours at from about 75 to 85° C., in the course of polymerization, to a polymerization vessel which contained 500 g of water. The initiator, 1 g of sodium persulfate dissolved in 100 g of water, was likewise supplied continuously in the course of the polymerization. To reduce the residual monomer content, a redox initiator (tert-butyl hydroperoxide/ascorbic acid) was then added and polymerization was continued.

To prepare the polymer salt, the batch was subsequently diluted with water, and the required amounts of oxides or hydroxides were added.

The resulting polymer solutions or polymer dispersions were finally spray-dried.

The copolymers prepared in this way are listed in Table 1 below.

TABLE 1

| Example | Monomers | Monomer ratio | Salt | Degree of neutralization |
|---------|----------|---------------|------|--------------------------|
| a | EA/MAS | 1:1 | Na | 35% |
| b | EA/MAS | 1:1 | Na/Ca = 1/6 | 35% |
| c | EA/MAS | 1:1 | Ca | 40% |
| d | EA/MAS | 1:1 | Na/Zn = 1/3 | 40% |
| e | EA/MAS | 1:1 | Zn | 40% |
| f | MMA/MAS | 2:1 | Na | 95% |
| g | MMA/MAS | 2:1 | Na/Ca = 1/6 | 85% |
| h | MMA/MAS | 2:1 | Na/Sr = 1/3 | 85% |
| i | tBA/MAS | 1:1 | K | 60% |
| j | MMA/MAS | 1:1 | Na/Zn = 1/4 | 45% |

EA = ethyl acrylate
MAS = methacrylic acid
MMA = methyl methacrylate
tBA = tert-butyl acrylate Example 2
(Preparing the dental prosthesis adhesive)

40 parts of the spray-dried powders 1a to 1j (particle size 5 to 200µ, water content 3.0% by weight) were intimately mixed at 25° C. with 20 parts of liquid paraffin (110–230 mPas) and 40 parts of vaseline (petrolatum from Riedel de Haen).

Example 3
(Comparing the adhesion with known dental prosthesis adhesives)

To determine the effectiveness of dental prosthesis adhesives 0.3 g of each test formulation was applied as uniformly as possible between two polymethyl methacrylate moldings and the tensile force required to separate the moldings was measured. The tensile force determined for all Examples 1a to 1j within a period of about 2 minutes was from 2700 to about 3000 cN. Tensile forces of more than 2640 cN have not been measured for any known adhesive creams.

We claim:

1. An adhesive for dental prostheses, comprising as its active adhesive partially or completely neutralized copolymers of from 5 to 95% by weight, based on the copolymer, of one or more acrylic esters of the formula I $$CH_2=CR'—COOR \qquad \text{I (monomer A)},$$

where R' is hydrogen or methyl and R is alkyl of 1 to 30 C atoms, and from 95 to 5% by weight of methacrylic and/or acrylic acid (monomer B).

2. An adhesive as defined in claim 1, wherein the copolymer is water-soluble.

3. An adhesive as defined in claim 1, wherein the copolymer is present as a uniform or mixed salt of sodium, potassium, calcium, magnesium, strontium or zinc.

4. An adhesive as defined in claim 1, wherein from 30 to 95% of the free carboxyl groups have been neutralized.

5. An adhesive as defined in claim 1, wherein the monomers (A) are $C_1$ to $C_4$ esters of acrylic or methacrylic acid.

6. An adhesive as defined in claim 1, wherein the copolymers comprise from 0 to 30% by weight, based on the copolymer, of further, free-radically polymerizable monomers (monomer C) selected from the group consisting of acrylamides, methacrylamides, N-vinyllactams, hydroxyalkyl acrylates, crotonic acid and maleic acid.

7. An adhesive as defined in claim 1, which comprises as active adhesive composition in addition to (a) conventional active adhesive compositions selected from the group consisting of partial salts of alkyl vinyl ether maleic acid copolymers, carboxymethylcellulose and salts thereof, polyvinylpyrrolidone or copolymers of vinylpyrrolidone and vinyl acetate, alginates, polyethylene glycols, polyethylene glycol copolymers, and mixtures thereof.

8. An adhesive as defined in claim 1, which comprises as active adhesive composition (a) a copolymer of
    from 20 to 80% by weight, based on the copolymer, of ethyl acrylate or methyl methacrylate and
    from 80 to 20% by weight of methacrylic or acrylic acid.

9. An adhesive for dental prostheses comprising: a copolymer of from 5 to 95% by weight of a monomer of the formula $$CH_2=CR'—COOR \qquad \text{I (monomer A)},$$

where R' is hydrogen or methyl and R is alkyl of 1 to 30 C atoms, and from 95 to 5% by weight of methacrylic and acrylic acid (monomer B), having a molecular weight of from 30,000 to 5 million daltons, and where all or some of the free carboxyl groups of the copolymer have been neutralized.

10. A process for preparing an adhesive for dental prostheses as defined in claim 1, which comprises copolymerizing
    (i) monomers A of the formula I $$CH_2=CR'—COOR \qquad \text{I (monomer A)},$$

where R' is hydrogen or methyl and R is alkyl of 1 to 30 C atoms, with monomers B selected from the group consisting of methacrylic and acrylic acid, the weight ratio of monomer A to monomer B being from 95:5 to 5:95,
    (ii) completely or partially neutralizing the resulting copolymer,
    (iii) drying the neutralized copolymer,
    (iv) mixing the dried polymer with a vehicle to form the prosthesis adhesive, and, optionally,
    (v) converting the resulting mixture into the powder form.

* * * * *

UNITED STATES PATENT AND TRADEMARK OFFICE
CERTIFICATE OF CORRECTION

PATENT NO.: 6,080,811

DATED: June 27, 2000

INVENTOR(S): SCHEHLMANN et al.

It is certified that error appears in the above-identified patent and that said Letters Patent is hereby corrected as shown below:

Col. 8, claim 10, line 55, "a" should be --an oil--.

Signed and Sealed this

Third Day of April, 2001

*Attest:*

NICHOLAS P. GODICI

*Attesting Officer*   *Acting Director of the United States Patent and Trademark Office*